Figure 1:
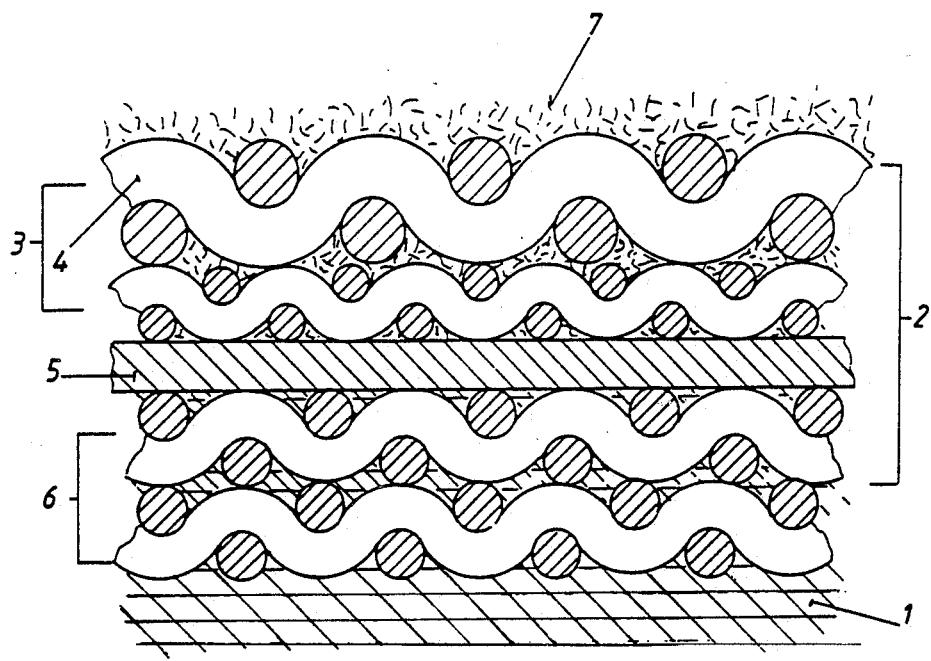

United States Patent [19]

Frey et al.

[11] Patent Number: 4,955,911
[45] Date of Patent: Sep. 11, 1990

[54] BONE IMPLANT

[75] Inventors: Otto Frey, Winterthur; Rudolf Koch, Berlingen, both of Switzerland

[73] Assignee: Sulzer Brothers Limited, Winterthur, Switzerland

[21] Appl. No.: 341,149

[22] Filed: Apr. 20, 1989

[30] Foreign Application Priority Data

Apr. 21, 1988 [CH] Switzerland ............ 1480/88

[51] Int. Cl.$^5$ .............................................. A61F 2/28
[52] U.S. Cl. ........................................ 623/16; 623/66
[58] Field of Search .................... 623/16, 18, 22, 23, 623/66

[56] References Cited

U.S. PATENT DOCUMENTS 4,479,271 10/1984 Bolesky et al. ................ 623/18

FOREIGN PATENT DOCUMENTS 0189546 8/1986 European Pat. Off. .............. 623/18
0190422 8/1986 European Pat. Off. .............. 623/18
0225838 6/1987 European Pat. Off. .
2539209 7/1984 France .

Primary Examiner—David J. Isabella
Attorney, Agent, or Firm—Kenyon & Kenyon

[57] ABSTRACT

The bone implant is formed of a plastic body having a multi-layer wire fabric secured to the outside surface. A separating layer is disposed between the wire fabric and two wire layers embedded within the plastic body. The separating layer serves to block the ingrowing bone tissue from contact with the plastic body while embedded layers are securely enveloped by the plastic of the body to prevent a break out of the fabric.

7 Claims, 1 Drawing Sheet

BONE IMPLANT

This invention relates to a bone implant. More particularly, this invention relates to a plastic bone implant.

Various types of bone implants have been known wherein the implant is made of a plastic body while a multi-layer wire fabric is disposed on the outside of the plastic body in order to provide a porous structure into which bone tissue may grow. For example, European Pat. application No. 0190422 describes a plastic bone implant with a multi-layer wire fabric on the outside of a plastic body which is anchored to at least one wire layer anchored in the plastic body. In such a construction, the pore sizes of the layers of the multi-layer fabric are of a size which increase in a direction away from the plastic body. However, it has been found in practice that the plastic-to-fabric bond may fail under heavy load. This appears to be caused by the wire layer in the plastic body not being satisfactorily enveloped by the plastic. As a result, the embedded layer may break out of the plastic body.

Accordingly, it an object of the invention to provide a plastic bone implant having a multi-layer wire fabric secured in a firm manner to an outside surface.

It is another object of the invention to improve the securement of a multi-layer wire fabric to a plastic body for a bone implant.

Briefly, the invention provides a bone implant which is comprised of a plastic body, at least two layers of wire fabric embedded in the plastic body, a multi-layer wire fabric disposed outside the plastic body and a separating layer secured to and between the embedded layers and the multi-layer wire fabric in order to block contact between the ingrowing bone tissue in the multi-layer fabric and the plastic body.

The layers which are embedded in the plastic body each have pore sizes of equal size. In addition, the pores of each layer are filled with the plastic of the body in order to be firmly anchored within the body.

The multi-layer wire fabric has pores of increasing size from layer-to-layer in a direction away from the plastic body for ingrowth of bone tissue.

The separating layer serves to block contact between the ingrowing bone tissue in the multi-layer fabric and the plastic of the plastic body. In this respect, the separating layer may have pores of a size less than the pores of the layers embedded in the plastic body. Alternatively, the separating layer may be made as a non-porous plate.

Advantageously, irrespective of the size of the fabric-to-plastic anchorage surface, the wire thickness of the layers anchored in the plastic body is at least 0.5 millimeters.

Where there are two anchoring layers in the plastic body, relatively thick plastic "bridges" arise between the wires of the fabric to inhibit a break-out of the fabric. As in a known construction, a regular pore structure having defined sizes can be provided only if the discrete layers are built up from wire fabric. Conveniently, in order to ensure very "straight" continuous pores through all the layers, each layer has filaments disposed at an angle of 45° relative to the filaments of the other layer in the plastic body. Likewise, each layer of the multi-layer wire fabric may have filaments disposed at an angle of 45° relative to the filaments of an adjacent layer.

A particular risk with "straight" pores of this kind, or in cases in which the plastic becomes a relatively thin viscous liquid, even if only briefly, during bonding to the wire fabric, is that a close-mesh lattice or grid cannot satisfactorily keep the plastic away from the multi-layer wire fabric outside the plastic body. In this case, the separating layer is in the form of a non-porous plate to positively block the flow of plastic into the wire fabric.

Figure 2:
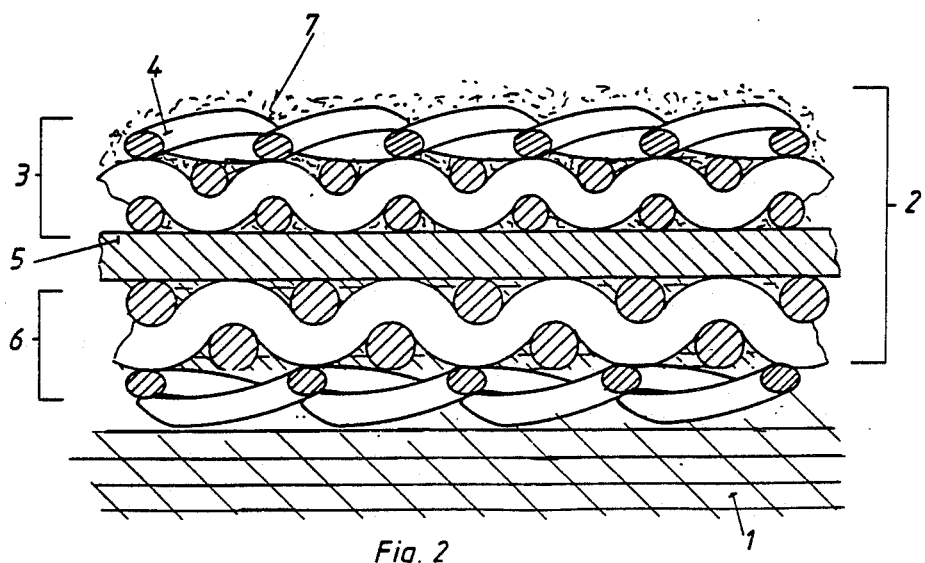

These and other objects and advantages of the invention will come more apparent from the following detailed description taken in conjunction with the accompanying drawings wherein:

FIG. 1 illustrates a part cross sectional view of a bone implant constructed in accordance with the invention; and FIG. 2 illustrates a cross sectional view similar to FIG. 1 wherein the direction of the filaments of adjacent layers are turned through 45° relative to one another.

Referring to FIG. 1, the bone implant which may be in the form of an acetabulum has a plastic body 1 covered by a structure 2 mainly comprised of a multi-layer wire fabric 3 of titanium or a titanium alloy. The multi-layer fabric 3 has pores in each layer of increasing size from layer-to-layer in a direction away from the plastic body 1 for the ingrowth of bone tissue 7 or to receive bone cement (not shown). The wire thickness of the wires 4 of the outer layers of the structure 2 determines the mesh size and therefore the pore size. As such, the wire thickness increases, as illustrated, in a direction away from the plastic body 1.

At least two layers of wire mesh 6 are embedded in the plastic body 1 with each having pore sizes equal to the pore sizes of the other layer. As indicated, all layers are parts of the structure 2.

In addition, a separating layer 5 is secured to and between the embedded layers and the multi-layer wire fabric 3 to block contact between ingrowing bone tissue 7 in the multi-layer fabric 3 and the plastic body 1. The separating layer 5 is in the form of a non-porous metal plate.

The embedded layers 6 have the same wall thicknesses and pore sizes and are both pressed into the polyethelene plastic body 1 to ensure a firm anchorage of the metal surface structure 2 in the plastic body 1. At the manufacturing of the implant all metal layers are bonded to one another, for example, by spot-welding before the structure 2 is pressed into the plastic body 1.

Alternatively instead using a non-porous plastic, the separating layer 5 may be form of a close-mesh wire fabric having a wire thickness and pore size smaller than those of the embedded layers 6 and the inner layer of the multi-layer wire fabric 3.

The continuity of the pores can be improved if the adjacent wire layers of the embedded layers 6 and the multi-layer fabric 3 are turned 45° relative to one another, for example as shown in FIG. 2. If more than two layers are present, the direction of rotation of a third layer is, of course, the same as the direction of rotation of the first layer.

The thicknesses of the wires 4, for example for the layers of the multi-layer fabric 3 is between 0.3 and 1.0 millimeters. If a fabric layer is also provided as the separating layer 5, the wires thereof have a diameter of from 0.1 to 0.3 millimeters. Irrespective of the plastic body 1 carrying the wire fabric, wire thicknesses of at least 0.5 millimeters have proved very satisfactory for the embedded layers 6 and give mesh sizes of approximately 1 millimeter.

In addition to titanium and titanium alloys, other elements known to be tissue compatible, such as tantalum, niobium, zirconium and alloys containing such elements can be used for the wire fabric. Another possibility is at least for the outer layers to have, in known manner, a coating, for example of titanium nitride or some other abrasion-resistance substance and/or a substance promoting the invasion of tissue.

Further, the wire fabric 3 may be provided with widened foundation surfaces by rolling before the discrete mesh layers are applied with a view to improving their bonding to one another, for example, by means of local metallurgical bonding. Bonding of this kind can be produced, for example, by spot diffusion welds.

The invention thus provides a bone implant particularly for use as an acetabulum wherein a multi-layer wire fabric can be secured to the outer surface of a plastic body of the acetabulum for the ingrowth of bone tissue or for implanting in a bone cement bed. At the same time, the separating layer between the multi-layer fabric and the embedded wire fabric layers serves to completely obviate contact between the living tissue and the plastic body.

The embedment of the fabric layers in the plastic body may be performed after the plastic body has been softened, for example by heating. Any suitable technique may be used for this purpose.

The invention further provides an implant wherein two layers of wire fabric are embedded in a plastic body in a secure manner so as to be enveloped by the plastic of the body to prevent a break out of the layers from the body.

What is claimed is:

1. A bone implant comprising:
   a plastic body;
   at least two layers of wire mesh embedded in a surface of said plastic body, each layer being of equal thickness to the other and having pore sizes equal to the pore sizes of the other layer with a mesh size of 1 millimeter, each layer having a wire thickness of at least 0.5 millimeters;
   a separating layer of non-porous material secured to one of said layers of wire mesh at said surface; and
   a porous multi-layer wire fabric secured to said separating layer, said multi-layer wire fabric having pores in said layers thereof of increasing size from layer-to-layer in a direction away from said separating layer for ingrowth of bone tissue.

2. A bone implant as set forth in claim 1 wherein said separating layer is a non-porous plate.

3. A bone implant as set forth in claim 1 wherein each layer of wire mesh in said plastic body has filaments disposed at an angle of 45° relative to the filaments of the other layer in said plastic body.

4. A bone implant as set forth in claim 1 wherein each layer of said multi-layer wire fabric has filaments disposed at an angle of 45° relative to the filaments of an adjacent layer of said multi-layer wire fabric.

5. A bone implant comprising
   a plastic body;
   at least two layers of wire mesh of equal thickness embedded in said plastic body, each layer having a wire thickness of at least 0.5 millimeters and pores of approximately 1 millimeter filled with plastic of said body to anchor said layers in said body;
   a porous multi-layer wire fabric disposed outside said plastic body, said multi-layer wire fabric having pores in said layer thereof of increasing size from layer-to-layer in a direction away from said body for ingrowth of bone tissue; and
   a non-porous separating layer secured to and between said embedded layers and said multi-layer wire fabric to block contact between ingrowing bone tissue in said multi-layer fabric and said plastic body.

6. A bone implant as set forth in claim 5 wherein said separating layer is a non-porous plate.

7. A bone implant as set forth in claim 5 wherein each layer of wire mesh in said plastic body has filaments disposed at an angle of 45° relative to the filaments of the other layer in said plastic body.

* * * * *

UNITED STATES PATENT AND TRADEMARK OFFICE
CERTIFICATE OF CORRECTION

PATENT NO.   : 4,955,911
DATED        : Sept. 11, 1990
INVENTOR(S)  : OTTO FREY, ET AL It is certified that error appears in the above-identified patent and that said Letters Patent is hereby corrected as shown below:

```
Column 1, line 23 change "it an" to -it is an-
Column 2, line 11 change "will come" to -will become-
Column 2, line 50 change "Alternatively instead" to
-Alternatively, instead-
Column 2, line 50 change "instead using" to -instead of using-
Column 2, line 51 change "form of" to -formed of-
```

Signed and Sealed this

Fifth Day of May, 1992

Attest:

DOUGLAS B. COMER

*Attesting Officer*   Acting Commissioner of Patents and Trademarks